(12) United States Patent
Harrison

(10) Patent No.: US 9,351,653 B1
(45) Date of Patent: May 31, 2016

(54) MULTI-CHANNEL RECONFIGURABLE SYSTEMS AND METHODS FOR SENSING BIOPOTENTIAL SIGNALS

(71) Applicant: Reid R. Harrison, Los Angeles, CA (US)

(72) Inventor: Reid R. Harrison, Los Angeles, CA (US)

(73) Assignee: Intan Technologies, LLC, Los Angeles, CA (US)

( * ) Notice: Subject to any disclaimer, the term of this patent is extended or adjusted under 35 U.S.C. 154(b) by 478 days.

(21) Appl. No.: 13/688,876

(22) Filed: Nov. 29, 2012

(51) Int. Cl.
*A61B 5/04* (2006.01)

(52) U.S. Cl.
CPC .................................. *A61B 5/04014* (2013.01)

(58) Field of Classification Search
CPC .... A61B 5/04; A61B 5/04004; A61B 5/0528; A61B 5/0476
See application file for complete search history.

(56) References Cited

U.S. PATENT DOCUMENTS

| | | | | |
|---|---|---|---|---|
| 5,206,602 | A * | 4/1993 | Baumgartner et al. | 330/9 |
| 2006/0173364 | A1* | 8/2006 | Clancy et al. | 600/485 |
| 2008/0180278 | A1* | 7/2008 | Denison | 340/870.18 |
| 2008/0312523 | A1* | 12/2008 | Dunseath | 600/383 |
| 2009/0306535 | A1* | 12/2009 | Davies et al. | 600/547 |
| 2010/0007413 | A1* | 1/2010 | Herleikson | 330/124 R |
| 2012/0095361 | A1* | 4/2012 | Xu et al. | 600/547 |

* cited by examiner

*Primary Examiner* — Sean Dougherty
(74) *Attorney, Agent, or Firm* — Kwan & Olynick LLP

(57) ABSTRACT

A biopotential monitoring device includes a configurable receiver circuit having a plurality of channels for receiving a plurality of biopotential signals from a biological tissue via a plurality of inputs coupled with the electrodes, and each channel substantially removes a DC (direct current) offset from a corresponding one of the biopotential signals and then band-pass amplifies such corresponding biopotential signal at a configurable gain and particular frequency range based on frequency control signals. The device further includes a controller circuit for receiving commands for configuring frequency characteristics of each biopotential signal. The controller automatically generates the frequency control signals based on such commands and outputs such frequency control signals to the configurable receiver circuit. The controller outputs a representation of each biopotential signal to an analyzer device that is configured to analyze such biopotential signal.

11 Claims, 9 Drawing Sheets

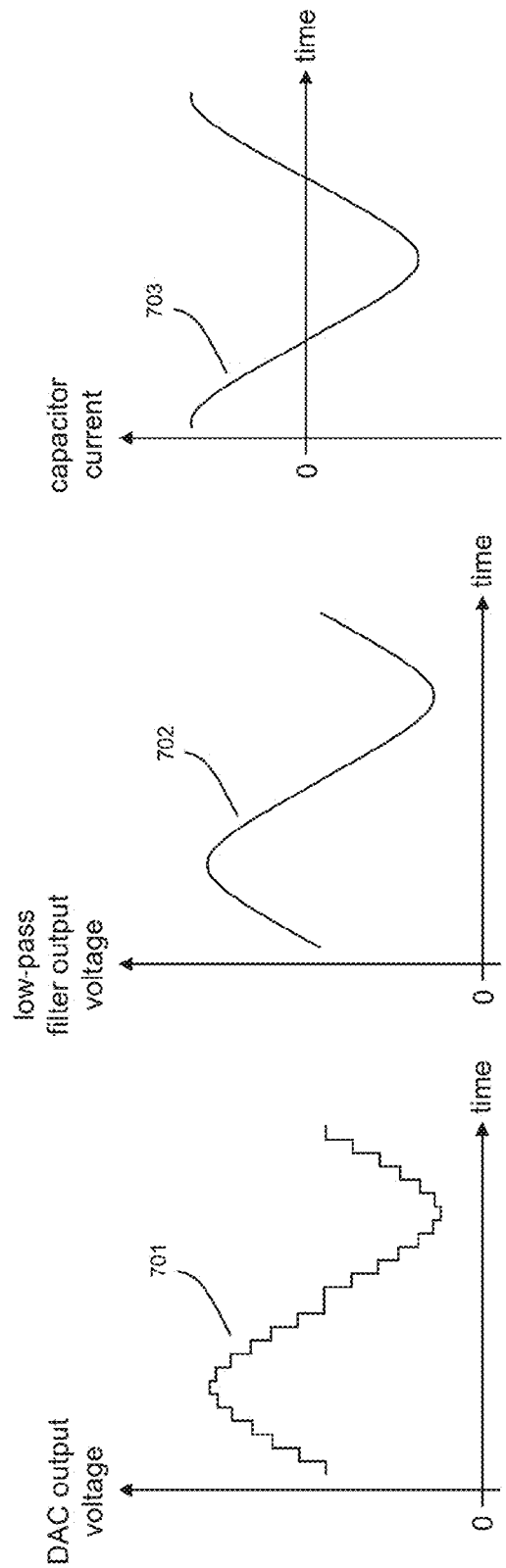

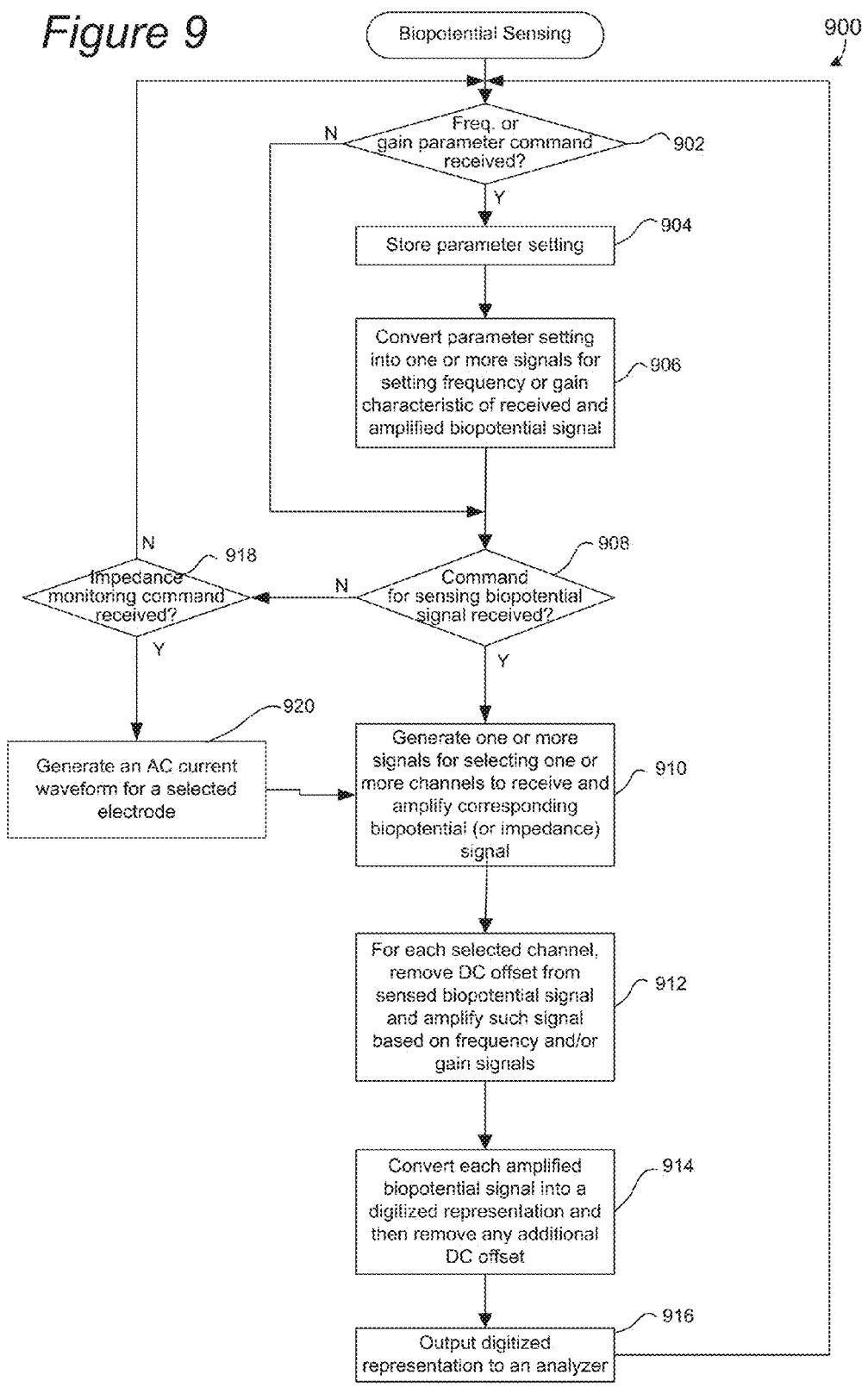

MULTI-CHANNEL RECONFIGURABLE SYSTEMS AND METHODS FOR SENSING BIOPOTENTIAL SIGNALS

TECHNICAL FIELD OF THE INVENTION

The present invention relates to integrated circuits for monitoring electrophysiological signals. More particularly, but without limitation, the present invention relates to a method and device for monitoring or sensing multiple biopotentials and monitoring the impedance of the sensing electrodes.

BACKGROUND

Biological tissues produce a wide variety of electrophysiological signals to convey information throughout the nervous system and to trigger muscle contractions. Sensing and monitoring these voltages or "biopotentials" is an important function for a wide variety of medical devices and scientific instruments. Examples of commonly observed biopotentials include the electroencephalogram (EEG) measured from the scalp; the electromyogram (EMG) measured in or near muscles; the electrocardiogram (ECG) measured on or near the heart; the electrocorticogram (ECoG) measured from the surface of the brain; local field potentials (LFPs) measured in the brain; and single-unit recordings of individual neurons in the brain or nerve fibers.

SUMMARY OF THE INVENTION

The following section presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a device for monitoring biopotentials of biological tissue through a plurality of electrodes is disclosed. This device includes a configurable receiver circuit having a plurality of channels for receiving a plurality of biopoential signals from a biological tissue via a plurality of inputs coupled with the electrodes, and each channel is configured to substantially remove a DC (direct current) offset from a corresponding one of the plurality of biopotential signals and then band-pass amplify such corresponding biopotential signal at a configurable particular frequency range based on one or more frequency control signals. The device further includes a controller circuit operable to receive commands for configuring or reconfiguring one or more frequency characteristics for receiving each biopotential signal. The controller is further configurable to automatically generate the one or more frequency control signals based on such commands and output such one or more frequency control signals to the configurable receiver circuit. The controller is further configurable to output a representation of each biopotential signal to an analyzer device that is configured to analyze such biopotential signal. In one example, the analyzer device is in the form of a computer or processor coupled via a bidirectional bus to the controller. In another example, the configurable receiver circuit and the controller circuit are integrated together on a single microchip.

In a specific implementation, the device further includes a multiplexer (MUX) coupled to the channels of the configurable receiver circuit so as to output a selected amplified biopotential signal based on a received channel select signal and an analog to digital converter (ADC) for receiving the selected amplified biopotential signal from the MUX and converting such signal to a digitized representation of such signal. The controller is further operable to output a channel selection signal to the MUX indicative of which channel the MUX is to output one of the biopotential signals to the ADC.

In a further aspect, the configurable receiver circuit comprises a configurable band-pass amplifier in each channel for amplifying the corresponding biopotential signal. The one or more frequency characteristics comprise a lower cutoff frequency and/or an upper cutoff frequency for each amplified signal. In this aspect, the receiver circuit also includes a capacitor at each input of each amplifier for removing the DC offset from each corresponding biopotential signal. In a specific example, the device also includes a digital high pass filter for receiving the digitized representation of the selected signal output from the ADC and removing one or more residual DC offsets introduced in such received digital representation based on a cutoff frequency signal received by the digital high pass filter. The one or more residual DC offsets include a DC offset that is introduced by the amplifiers, MUX, or ADC, and the commands further include a command for reconfiguring a cutoff frequency for the digital high pass filter. In this example, the controller is further configurable to automatically generate a cutoff frequency control signal based on the command for reconfiguring the cutoff frequency and outputting such cutoff frequency control signal to the digital high pass filter.

In a further aspect, the commands include a command for reconfiguring a gain of each biopotential signal input to each amplifier so that the amplified signal output from each amplifier has a signal level that falls within the range of the ADC. In another implementation, the ADC has a resolution that is between 10 to 16 bits.

In a further embodiment, the device also comprises an impedance measurement module for generating a capacitively-coupled AC (alternating current) current waveform, having an amplitude and frequency, that is applied to a particular input coupled to a particular channel to measure impedance of a corresponding particular one of the electrodes. In this embodiment, the impedance is determined by measuring a voltage signal received at the particular channel in response to the AC current waveform applied to the particular input. In a further aspect, the controller is further configured to receive a plurality of commands for reconfiguring the amplitude and frequency of the AC current waveform generated by the impedance measurement module, and the controller is further configurable to automatically generate one or more AC waveform control signals based on the commands for reconfiguring the amplitude and frequency and to output such one or more AC waveform control signals to the impedance measurement module.

In another implementation, the controller is further configured to receive a plurality of commands for reconfiguring the amplitude and/or frequency so as to generate a plurality of AC current waveforms for performing impedance spectroscopy. In yet another example, the impedance measurement module comprises a digital to analog converter (DAC) having an input for receiving a plurality of digital voltage values based on a first one of the AC waveform control signals, and the DAC is operable to convert such digital voltage values into a plurality of analog voltage values and output such analog voltage values. The impedance module also comprises a low pass filter having an input for receiving the plurality of analog voltage values output by the DAC, and the low pass filter is operable to attenuate frequencies that are higher than a predefined value so as to output an AC voltage waveform, which is based on the received analog voltage values, to the particular input that is coupled to the particular electrode. The impedance module further comprises one or more capacitors coupled to the output of the low pass filter and arranged to receive a second one of the AC waveform control signals that sets a capacitance value of the one or more capacitors so as to convert the AC voltage waveform into an AC current waveform having substantially all DC current removed from the AC current waveform that is input into the particular electrode.

In another embodiment, the invention pertains to a method of monitoring biopotential of biological tissue through a plurality of electrodes. The method comprises (i) receiving a plurality of commands into a biopotential sensing device, wherein the commands include commands for setting a high and low cutoff frequency and for selecting one or more channels for outputting biopotential measurements; (ii) the biopotential sensing device sensing a biopotential signal from each of a plurality of electrodes coupled to a plurality of channels of the biopoential sensing device; and (iii) the biopotential sensing device band-pass amplifying each biopotential signal based on the high and low cutoff frequency and outputting a digital representation of the band-pass amplified biopotential signal with substantially zero DC offset for each selected channel. In a specific method embodiment, the commands further include a command for setting a gain and wherein the biopotential sensing device amplifies each biopotential signal based on the gain. In further aspects, the method includes operations for using one or more features of the device described above.

In an alternative embodiment, a biopotential sensing system includes a plurality of electrodes for attaching to biological tissue, a biopotential sensing system communicatively coupled to the electrodes, and an analyzer system for controlling the biopotential sensing system. The analyzer system includes at least one processor and memory that are configured to send a plurality of commands to the biopotential sensing device, and the commands include commands for selectively setting a high and low cutoff frequency and for selecting one or more channels for outputting biopotential measurements by the biopotential sensing system. The analyzer system is further configured to analyze such biopotential measurements. The biopotential sensing device is configured to sense a biopotential signal from each of the electrodes and band-pass amplify each biopotential signal based on the high and low cutoff frequency and output a digital representation of the band-pass amplified biopotential signal with substantially zero DC offset for each selected channel. In further aspects, the biopotential sensing device has one or more features as described above.

These and other features of the present invention will be presented in more detail in the following specification of certain embodiments of the invention and the accompanying figures which illustrate by way of example the principles of the invention.

BRIEF DESCRIPTION OF THE DRAWINGS

FIG. 7A-7C illustrates typical signals in various stages of the sub-circuit from FIG. 3 that generates AC (alternating current) current waveforms for electrode impedance measurement.

FIG. 9 is a flowchart illustrating one embodiment of a process for biopotential sensing using embodiments of the sensing device described herein.

DETAILED DESCRIPTION OF THE SPECIFIC EMBODIMENTS

Figure 1:
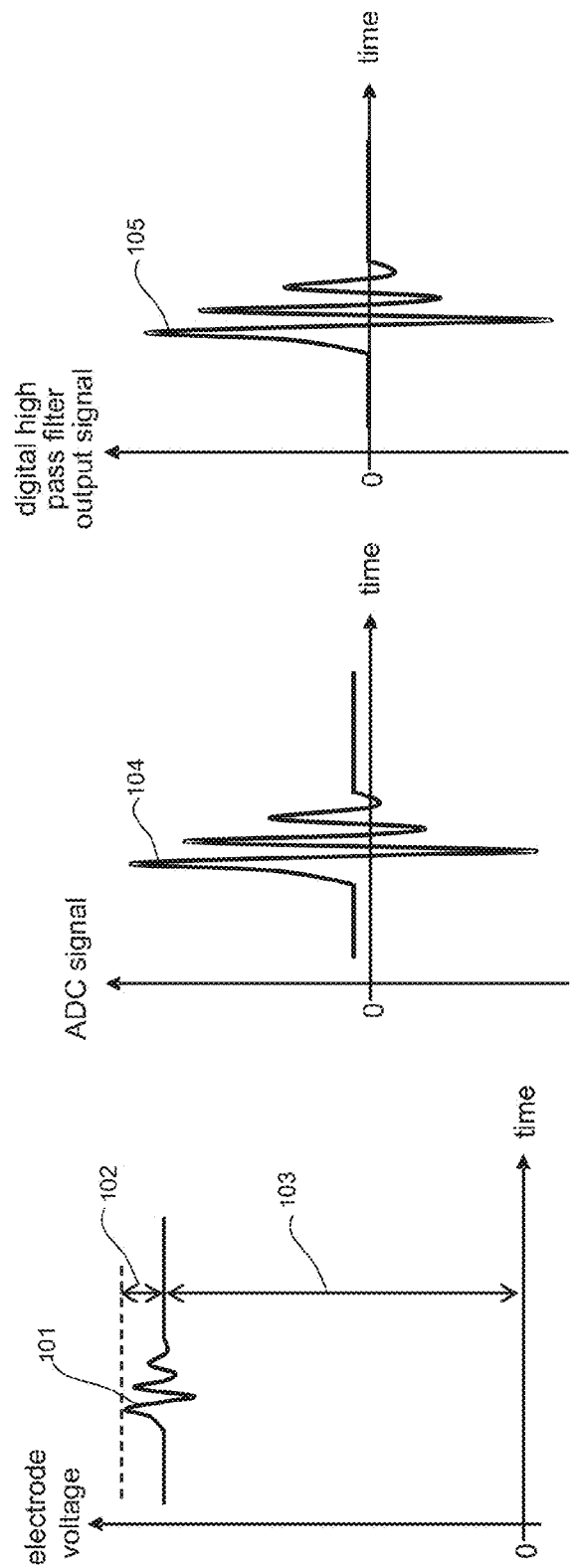
FIG. 1A illustrates the characteristics of a typical "raw" biopotential signal before amplification and filtering.
FIG. 1B illustrates the characteristics of a typical biopotential signal after amplification and analog band-pass filtering.
FIG. 1C illustrates the characteristics of a typical biopotential signal after amplification, analog band-pass filtering, and digital high pass filtering to remove all DC (direct current) offset.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction:

Many medical monitors and scientific instruments require devices capable of amplifying small analog voltage fluctuations, converting them to a digital data stream, and transferring this information to an analyzer system for processing and/or storage. For example, many prosthetic arms and hands sense surface EMG signals from bicep, tricep, or pectoral muscles and use the amplitude or envelope of EMG activity to control motors in an artificial elbow, wrist, and/or hand. Other example biopotential signals include EEG measured from the scalp, ECG measured on or near the heart, ECoG measured from the brain's surface, and LFP signals measured from individual neurons or nerve fibers.

Neural recording instruments using high-density microfabricated multi-electrode arrays detect neural action potentials, or "spikes", by monitoring the amplitude of signals in a limited frequency band. These signals may be recorded or used for real-time control of brain-computer interfaces.

The extracellular electrodes used to monitor electrophysiological signals may either penetrate tissue or rest on the surface of the skin or other organ. The magnitudes of these biopotentials typically range from about 1 microvolt to 5 or 10 millivolts. Voltages this small are typically amplified before they can be accurately digitized using an analog-todigital converter (ADC). However, the electrochemistry of the electrode-tissue interface introduces offset voltages that are typically in the range of tens to hundreds of millivolts, and these offset voltages can be orders of magnitude larger than the amplitude of the biopotential signals.

The frequency content of biopotential signals also varies with electrode size and recording location. For example, microelectrodes that penetrate brain tissue can detect both local field potentials (LFPs) ranging from 1 Hz to around 200 Hz and neural "spikes", or action potentials with frequency content from around 200 Hz to 5 or 10 kHz. Electroencephalogram (EEG) electrodes placed on the scalp typically detect useful signals at frequencies between 0.1 Hz to 200 Hz. Electrocardiogram (ECG) electrodes typically observe signals in the range of 0.5 Hz to 100 Hz.

The quality of biopotential signals is a function of electrode impedance. In general, the impedance of an electrode in contact with biological tissue varies with frequency and can change over time as the body reacts to contact with a foreign body. Surface electrodes change impedance in the presence of sweat, or as the adhesive holding them to the skin weakens or fails. The impedances of chronically implanted electrodes change in response to immune system reactions or the growth of scar tissue over time.

Programmable Biopotential Sensing Systems and Methods

In general, certain embodiments of the present invention provide a programmable biopotential sensing device for blocking the DC (direct current) electrode offset of a biopotential signals measured from a plurality of electrodes, dynamically adjusting gain, lower cutoff frequency, and upper cutoff frequency of such biopotential signals, and monitoring impedance levels of such biopotential signals in a diverse number of applications. In a specific implementation, the biosensing device takes the form of a software-reconfigurable (e.g., programmable) integrated circuit (microchip) device for biopotential monitoring and impedance measurement through a plurality of peripheral (off-chip) electrodes.

In an integrated circuit device implementation, an integrated biosensing device comprises a receiver circuit having a plurality of channels for receiving corresponding measured signals. Each channel blocks the DC electrode offset of the corresponding measured signal. In this embodiment, the receiver circuit also comprises an array of programmable band-pass amplifiers for which gain, lower cutoff frequency, and upper cutoff frequency are reconfigurable, although these values can remain fixed in other embodiments. In a particular aspect, the biosensing device also includes a multiplexed analog-to-digital converter (ADC) to digitize the amplified and filtered biopotential signals and an area-efficient digital high-pass filter to completely remove any residual DC offset added by the analog front-end electronics.

The device also may include an impedance measurement module, for example, in the form of a digital-to-analog converter (DAC) and associated analog electronics, to generate a capacitively-coupled AC (alternating current) current that can be steered to a selected input wire for the purposes of measuring the impedance of the electrodes connected to the chip. Communication with the device can be mediated through a bidirectional digital serial bus that uses a small number of wires to simultaneously receive commands and transmit digitized biopotential signals between the chip and an analyzer system, such as a computer or other digital controller.

In a typical application, a plurality of electrodes can be connected to the microchip, and these electrodes can be attached to electrically active biological tissue. The microchip can be connected to an analyzer system, such as a computer, microcontroller, FPGA (field programmable gate array), or other digital device, for example, via a four-wire digital serial bus. The analyzer system can be configured to command the microchip to digitize each amplifier channel in rapid succession, e.g., round-robin fashion, and the data describing the biopotential waveform from each electrode may then be relayed back to the analyzer system for analysis and/or storage. The analyzer system can also be configured to send commands to the microchip to configure the lower and upper bandwidth of the amplifiers so as to match the frequency content of the biopotentials of interest. The analyzer system can also be configured to send commands to change the gain of the amplifiers to scale the biopotentials so as to match the full range of the ADC.

The analyzer system can also be configured to set the cutoff frequency for a digital high-pass filter that removes any residual offset introduced by the amplifiers or ADC. When this filter is implemented digitally, such filter is not subject to mismatch or offset and, thus, ensures that all biopotential signals sensed by the microchip will have a DC level of substantially zero. Generating "zero-mean signals" allows the analyzer system to easily analyze the amplitudes of signals from the chip and set appropriate threshold levels for event capture (e.g., neural action potential detection) or measure signal envelope (e.g., for EMG control of prosthetic devices).

To measure electrode impedance, the analyzer system can be configured to also issue commands to the microchip so as to generate an AC current of a particular frequency and magnitude. The generated current can be directed to one input wire at a time. This directed current can then flow into the electrode that is connected to this particular input wire. The current flowing into the selected electrode will generate a voltage proportional to its impedance, and this voltage fluctuation can then be sensed through the amplifier channel, just like any other signal. The analyzer system can be configured to then isolate the frequency component in the selected waveform corresponding to the frequency of the AC current, estimate the voltage magnitude at this frequency, and calculate electrode impedance from this calculated voltage magnitude (and the known current magnitude).

By using a DAC to generate the impedance test waveform, the sensing system is capable of generating a wide variety of arbitrary waveforms, including sine waves of different frequencies. The ability to test the impedance of electrodes at different frequencies (e.g., impedance spectroscopy) provides more information on the state of the electrode and electrode-tissue interface than measuring impedance at a single frequency. By using capacitors to couple the DAC to the electrode under test, it can be guaranteed that substantially no DC current will flow into the electrode, even if an unforeseen event causes the analyzer system issuing commands to the sensing system to freeze in the middle of an impedance measurement operation. This guarantee of substantially zero DC current into the electrodes can serve to protect the integrity of both electrodes and biological tissue.

Figure 2:
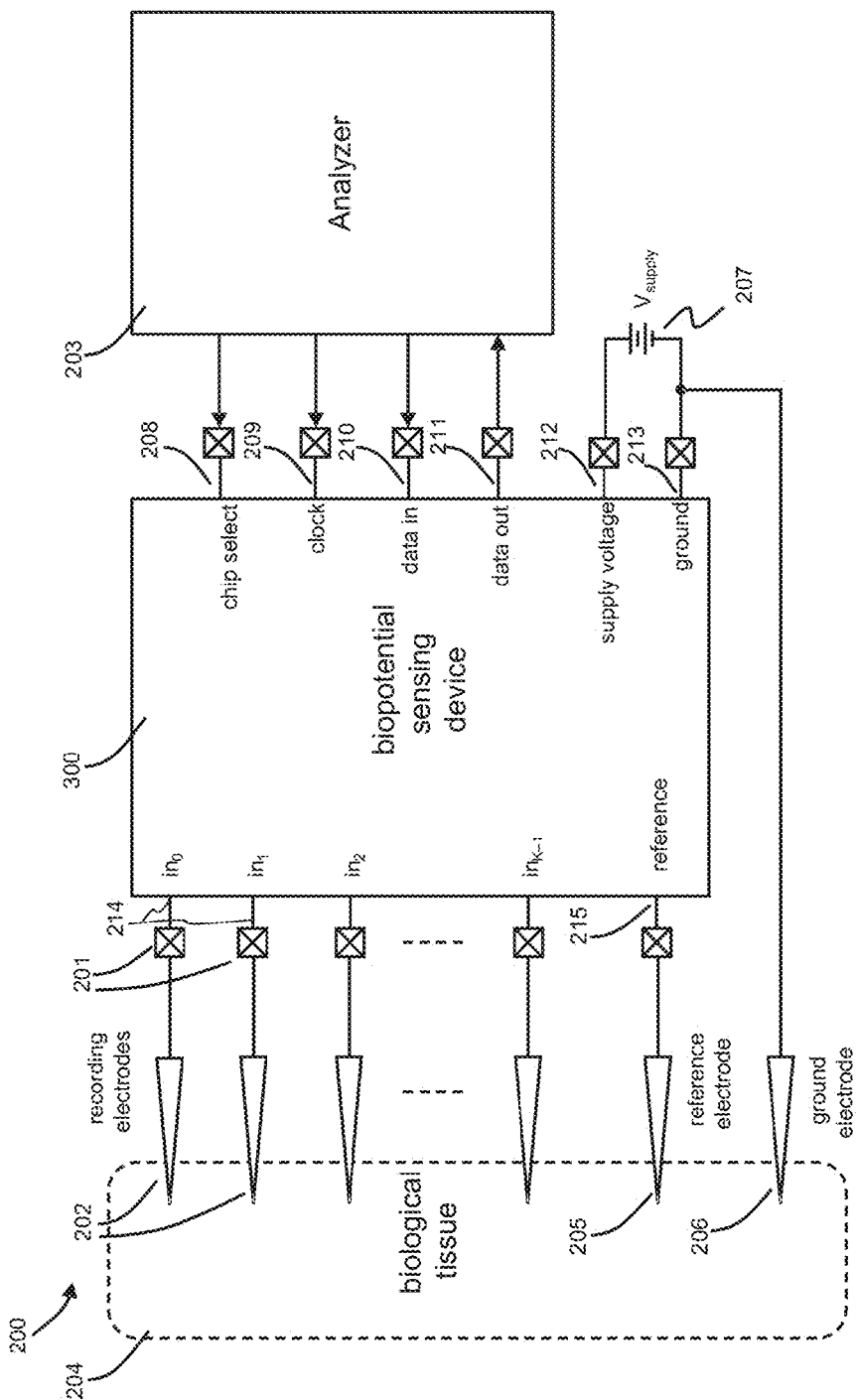
FIG. 2 is a block diagram of an electrophysiology monitoring system in accordance with a specific implementation of the present invention.

FIG. 2 is a block diagram of an electrophysiology monitoring system in accordance with a specific implementation of the present invention. As shown, biopotential signals of biological tissue (204) may be detected by monitoring the voltages on a plurality of recording electrodes (202) relative to the voltage on a reference electrode (205). The tissue can be held at approximately the same potential as the monitoring electronics by using a ground electrode (206), which is sometimes shorted to the reference electrode (205). In some applications, a single grounded reference electrode is used. The small voltage waveforms present on the electrodes are generally conditioned and digitized by an integrated monitoring or sensing circuit (300), incorporating a particular implementation of the present invention.

Although the monitoring circuit (300) is described herein as being integrated on a single chip, the monitoring circuit can be integrated or implemented on any number of chips or components. Although specific bus configurations are described herein, any suitable number and type of control signals may be generated by any number of components and outputted to control any number of operating parameters of one or more components of the sensing system. For example, any suitable type of communication lines, such as parallel or serial buses using any suitable communication protocol, may be used.

In the illustrated example, all input/output signals for the monitoring circuit are connected to the integrated circuit (300) via metal bond pads (201) built into the top of the integrated circuit. Any suitable type of bonding may be used to couple the monitoring circuit (300) with various input/output with respect to other components, such as electrodes and a controller or analyzer device. Examples of suitable types of bonding may include wedge, ball, tape-automated, etc., and examples of suitable types of conductive material that may be used for the wiring or bonding site material may include doped or undoped conductive materials, such as aluminum, copper, gold, palladium, silver, various conductive alloys, etc.

The small analog voltages from the electrodes may be conveyed to the integrated sensing circuit (300) by any suitable transmission medium, such as wires carrying the signals from K recording electrodes (214) (numbered zero through K−1) and the reference electrode (215). Typical values of K are 16, 32, or 64, but the integrated circuit may in general contain circuitry to interface with any number of electrodes. Power may be delivered to the integrated sensing circuit (300) from a battery or other DC power supply (207) through supply (212) and ground (213) wires. Example DC power supply values have a range of between about 1.0 and 5.0 V.

The integrated circuit (300) may be communicatively coupled with an analyzer system (203), such as a remote computer, microcontroller, or other digital system, for example, via a bidirectional digital serial bus having a 'chip select' signal (208) to permit multiple chips to share one bus; a 'clock' signal (209) to sequence the serial data conveyed over the bus; a 'data in' signal (210) used to send commands for initiating monitoring activities and reconfiguring one or more operating parameters of the integrated sensing circuit (300); and a 'data out' signal (211) used to send digitized biopotential data from the integrated sensing circuit (300) to the analyzer (203) for analysis, storage, or transmission. Each of these digital signals may be a single wire carrying a digital 'low' or 'high' voltage, or a pair of wires carrying a differential digital voltage (e.g., the common +/−350 mV low-voltage differential signaling (LVDS) protocol).

The analyzer (203) may be operable to send commands to the biopotential sensing device (300) to configure the signal conditioning properties of the device (e.g., amplifier gain and bandwidth) to match the expected frequency content and amplitude of the biopotential signals in a particular application. After the sensing device (300) has been configured, the analyzer (203) may then command the device to perform an analog-to-digital conversion on a biopotential signal received on a particular electrode. By repeating this command for each electrode connected to the sensing device and then repeating this procedure in loop, the analyzer system can acquire digitized waveforms from all K electrodes. Based on the observed waveforms, the analyzer system may be operable to reconfigure the gain or bandwidth of the amplifiers on the sensing device. The analyzer system can also be configured to send commands to monitor electrode impedances on any of the electrodes (202).

Figure 3:
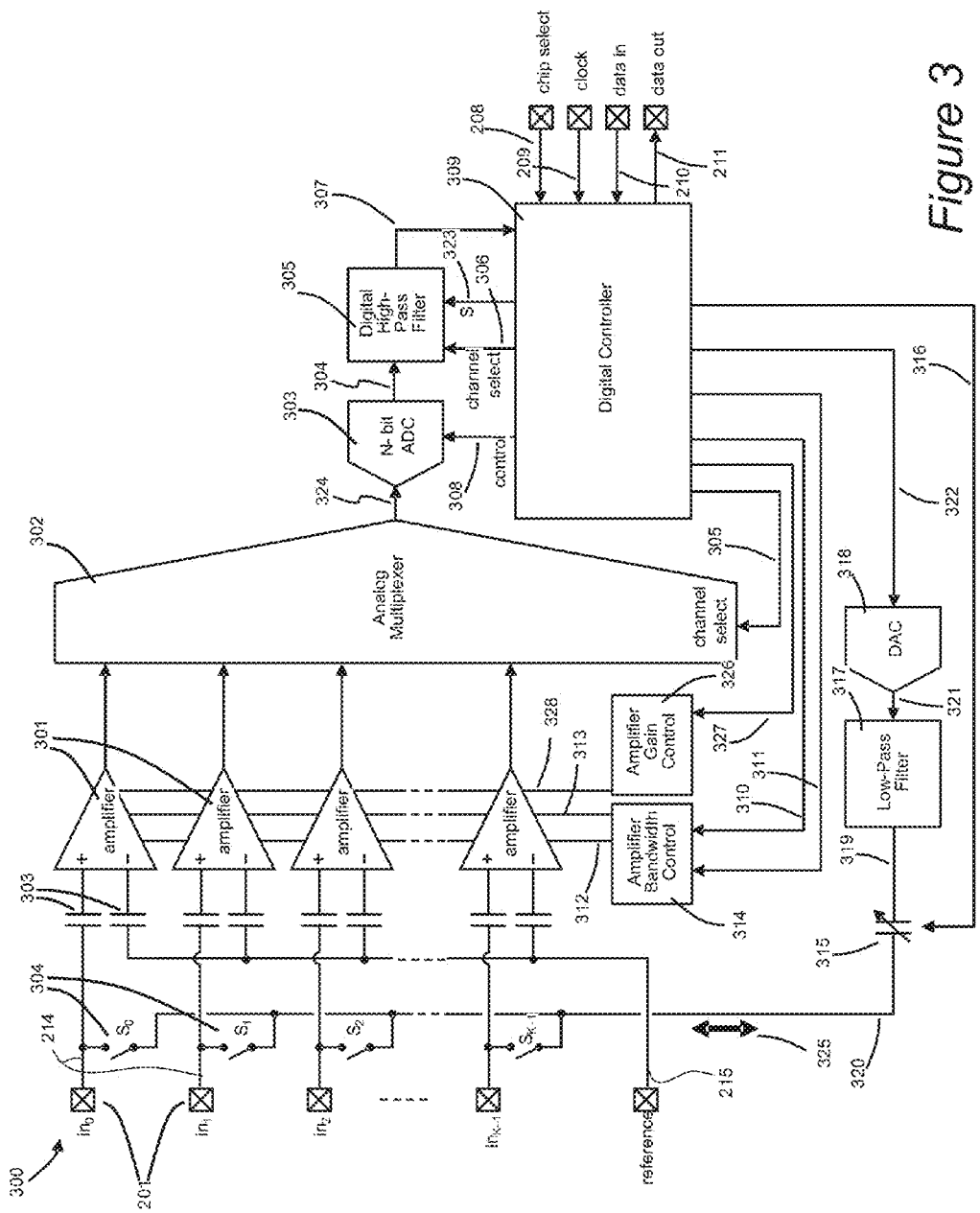
FIG. 3 is a diagram of an example embodiment of a reconfigurable biopotential sensing integrated circuit according to one embodiment of the present invention.

FIG. 3 is a block diagram of the reconfigurable biopotential sensing integrated circuit (300) according to one embodiment of the present invention. In certain embodiments, all the components of FIG. 3 reside on one microchip and any input/output signals pass through standard metal bond pads (201) that may include circuitry for protecting the on-chip electronics from electrostatic discharge (ESD) events. The biopotential signals read from the recording electrodes may be conveyed on input wires (214) to integrated series capacitors (303) that substantially block any DC offset present on the electrode. Typical values of each capacitor would be in the range of about 1 pF to 100 pF.

After each series capacitor (303), the signal may then be passed to the positive input of a band-pass amplifier (301). The signal from the reference electrode (215) may also be passed through series capacitors (303), to the negative input of a band-pass amplifier (301). Each band-pass amplifier (301) can be generally designed to have low input-referred noise (e.g., less than ten microvolts root-mean-square (rms) across its bandwidth). The lower and upper cutoff frequency of each amplifier (301) may be controlled by the signals on two lines, respectively: the lower cutoff frequency control line (312) and the upper cutoff frequency control line (313). The amplifier bandwidth control circuit (314) may be configured to generate these signals and distribute them to all amplifiers (301) that receive a sensed biopotential signal on the microchip. Additionally, the gain of each amplifier (301) may be controlled by the signal on the gain control line (328). The amplifier gain control circuit (326) may be operable to generate this gain control signal and distribute such gain control to all amplifiers (301) that receive a sensed biopotential signal on the microchip. Both the bandwidth and gain control circuits may generally convert the low and upper cutoff frequency and gain values, respectively received from the controller (309) into the appropriate input signals to cause the amplifiers (301) to achieve such values.

Figure 4:
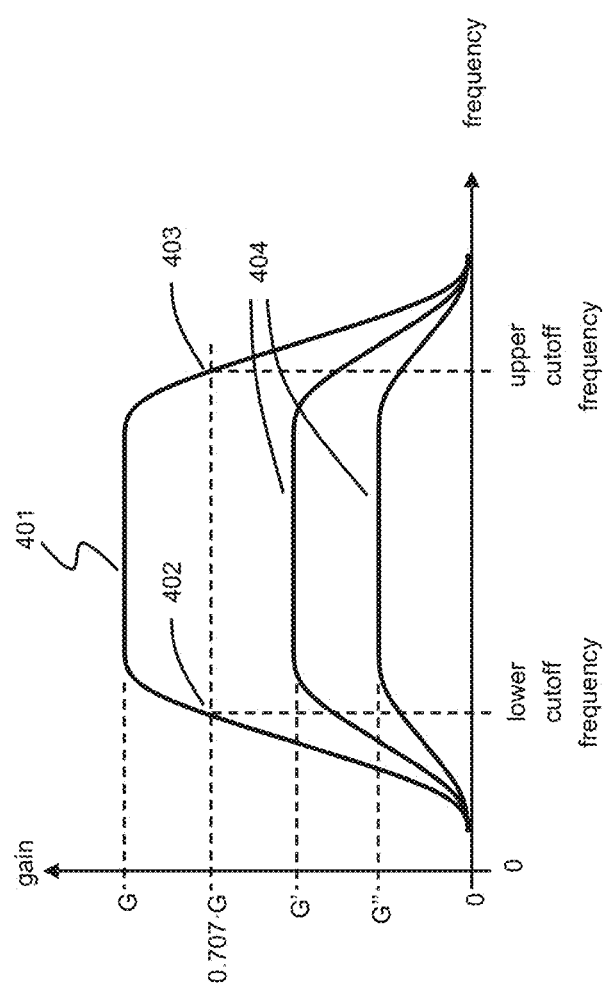
FIG. 4 is a diagram illustrating the frequency response of the amplifiers shown in FIG. 3.

FIG. 4 illustrates the frequency response of the band-pass amplifier (301) of FIG. 3. The pass band (401) of the amplifier has a nearly constant gain G. The lower cutoff frequency (402) and upper cutoff frequency (403) are defined as the points, where the gain drops below the pass-band gain G divided by a factor of the square root of two (e.g., 0.707·G). To match the characteristics of a wide variety of biopotentials, the lower cutoff frequency can be reconfigurable over a range of approximately 0.1 Hz to 200 Hz, and the upper cutoff frequency can be reconfigurable over a range of approximately 100 Hz to 10 kHz. The gain of the amplifier may be fixed or variable. Variable gains of G' and G" are depicted (404). In typical biopotential applications, amplifier voltage gains could vary between 50 V/V and 1000 V/V. In some applications, a constant gain may be sufficient to cover a broad range of biopotentials.

Each band-pass amplifier (301) and its corresponding input capacitors (303) are referred to herein as a recording "channel." Referring back to FIG. 3, the output signal from each channel of the bank of band-pass amplifiers (301) can be tied to the input wires of an analog multiplexer (302). The multiplexer can be operable to select a signal from one of its K inputs and passes such signal to an N-bit ADC (303), which would typically have a resolution of between 10 to 16 bits (N=10-16). Exceptionally high ADC resolution (e.g., N>16) is not necessary because the gain of the amplifiers (301) may be adjusted to boost small signals. Lower gains may be used in applications sensing large biopotential signals to avoid saturating the ADC. Thus, a low-power, Nyquist-rate, successive-approximation register (SAR) ADC may be used in embodiments of the present invention. A digital controller (309) may be configured to select which amplifier channel will pass through the analog multiplexer (302) to the ADC (303) by placing a binary number ranging between zero and K-1 on a 'channel select' bus (305). After an amplifier channel has been selected and the analog multiplexer passes the appropriate amplifier output to the ADC, the digital controller may send control signals (308) to the ADC to initiate an analog-to-digital conversion. The ADC converts the analog voltage at its input (324) into an N-bit binary number on an output bus (304).

Even though the DC electrode offset has been blocked completely by the series capacitors (303) at the input of the amplifiers (301), more DC offsets and low-frequency drift will have likely accumulated from fabrication imperfections in the amplifiers (301), the analog multiplexer (302), and the ADC (303). Small DC offsets (on the order of a few millivolts) in integrated analog circuits commonly result from device mismatch. For example, any two nominally identical MOS transistors will have slightly different threshold voltages after fabrication. To completely eliminate these additional DC offsets and drift, the monitoring system 300 may include a digital high-pass filter (305) to provide numerically ideal offset elimination and ensure that the baseline level of each digitized biopotential signal is precisely zero. Ensuring that each digitized biopotential signal has a zero baseline level reduces the amount of signal processing that must be performed by the analyzer (203) to extract application-relevant features such as amplitude or envelope.

Typical signals at three points in the system are illustrated in FIG. 1A-1C. FIG. 1A shows a voltage vs. time representation of a typical raw voltage (101) sensed by an electrode in biological tissue (204). The electrode-tissue interface usually introduces an offset voltage (103) that is many times larger than the amplitude of the AC biopotential signal (102). After blocking the electrode offset, the biopotential sensing system 300 amplifies, band-pass filters, and digitizes the signal (102), producing the signal (104) as shown in FIG. 1B. While the large DC offset associated with the electrode-tissue interface has been removed, other small DC offsets have been introduced by transistor mismatch and other fabrication imperfections in the analog band-pass amplifier circuits, the multiplexer, and the ADC. To remove all offset and achieve a true "zero baseline" signal, the digitized signal may be passed through a digital high-pass filter, yielding the signal (105) shown in FIG. 1C. Typical DC offsets that may be introduced by the amplifiers, MUX, and/or ADC and removed by the high pass filter have a range between about 1 mV and 200 mV.

Referring back to the illustrated embodiment of FIG. 3, digital controller (309) may be configured to use two buses to pass (in binary format) two variables to the digital high-pass filter module (305): the amplifier channel that has been selected (306) (e.g., the same value as the channel select bus (305)); and a variable S (323) that selects the cutoff frequency to be applied by the digital filter (305). The digital filter (305) is operable to attenuate all frequencies below the cutoff frequency specified by S (323) and completely block any DC component of the signal from any channel. (Embodiments of the digital high-pass filter (305) operation will be described in more detail below.) The output of the digital filter (305) can be a bus (307) carrying an N-bit binary number representing the digitized value from the selected amplifier channel after digital filtering to remove residual offsets. The digital filter (305) may also pass output value (307) back to the digital controller (309), which can relay this signal back to the analyzer (203) for analysis and/or recording. Alternatively, the digital filter may directly pass this output value (307) to the analyzer (203).

The digital controller (309) may be communicatively coupled with an analyzer system (203), such as a remote computer, microcontroller, or other digital system through any suitable communication mechanisms, such as bidirectional serial bus ((208), (209), (210), (211) (as also shown in FIG. 2), a bidirectional parallel bus, etc. The 'chip select' signal (208), 'clock' signal (209), 'data in' signal (210) are input to the controller (309) from the analyzer system (203) via this bus, and the 'data out' signal (211) is output from the controller (309) to the analyzer system (203) via this bus.

The 'chip select' signal (208) permits multiple microchips to share the same serial bus. Any commands sent to a particular microchip are ignored unless the 'chip select' signal (208) for such particular microchip is asserted. The 'clock' signal (209), along with the 'chip select' signal (208), provide a complete system clock for the digital controller (309). No additional clock or oscillator is needed to control the ADC (303) or other components of the chip.

Commands may be conveyed to the digital controller (309) through the 'data in' line (210). This 'data in' signal may be sampled on each clock cycle. For instance, a 16-bit number can be transmitted to a receiving microchip in 16 clock cycles. Of course, if a parallel bus is used, each bit can be simultaneously transmitted in a single clock cycle. The digital controller (309) can be operable to interpret and execute the received commands. The monitoring device can be commanded to sample a particular amplifier channel using the ADC (303), reconfigure the gain or bandwidth of the band-pass amplifiers (301), set the cutoff frequency of the digital filter (307), or operate circuitry for electrode impedance measurements (which will be discussed below). When a command is being clocked into the device, the result of a previous command (e.g., to sample a particular channel) may be simultaneously clocked out of the 'data out' line (211). Alternatively, the 'data out' signal may be clocked out via the 'data out' line (211) prior to or after a next command is received via the 'data in' line (210) In sum, any suitable communication standard or protocol may be implemented, such as the standard four-wire serial peripheral interface (SPI) protocol, which allows the monitoring device to easily interface with many standard computers and microcontrollers. Other communication protocols may include I$^2$C, CAN, USB, PCI (peripheral component interface), PCI express, PCI-X, AGP (accelerated graphics port), VLB (VESA local), EISA (extended industry standard architecture), etc.

In response to commands from analyzer system (203), the digital controller (309) can change the value of binary numbers on a bus leading to the amplifier bandwidth control circuit (314) or amplifier gain control circuit (326). In one embodiment, the lower cutoff frequency bus (311) conveys a binary number that the amplifier bandwidth control circuit (314) converts into a signal on the lower cutoff frequency control line (312) that then sets the lower cutoff frequency of each amplifier (301). Similarly, the upper cutoff frequency bus (310) may convey a binary number that the amplifier bandwidth control circuit (314) converts into a signal on the upper cutoff frequency control line (313) that then sets the lower cutoff frequency of each amplifier (301). The amplifier gain bus (327) may convey a binary number that the amplifier gain control circuit (326) converts into a signal on the amplifier gain control line (328) that then sets the gain of each amplifier (301). The bandwidth and gain of the amplifiers (301) can therefore be reconfigured to match the biopotential signals of interest by issuing one or more digital commands.

The monitoring system may also be operable to monitor electrode impedance. For instance, the amplifiers (301) may also be used to measure electrode impedance at a particular frequency f. If an AC current at frequency f is injected onto one of the input wires (214) connecting to a peripheral electrode (202) via a bonding pad (201) and the impedance of the series capacitor (303) is much greater than the impedance of the electrode, then most of the current will flow into the electrode (202) and produce an AC voltage with a magnitude proportional both to the magnitude of the current and the impedance of the electrode. Said in another way, the magnitude of the complex impedance Z is equal to the voltage magnitude divided by the current magnitude. If the magnitude of the current is known, then the electrode impedance can by calculated by measuring the amplitude of the signal component at frequency f Frequency ranges that can be used for impedance measurements can include frequencies within the range of about 1 Hz to 10 kHz.

To facilitate impedance monitoring, the monitoring system (300) may also include a mechanism for generating an AC waveform of known magnitude and frequency and for directing this current to one selected electrode for impedance measurement. For example, a digital-to-analog converter (DAC) (318) generates an output voltage (321) that may be set by a digital signal (322) from the digital controller (309). Commands from the analyzer (203) can update this bus regularly or periodically to create an arbitrary AC waveform, such as an approximation of a sine wave with a particular frequency and amplitude, at the DAC output (321).

FIG. 7A-C shows typical AC waveforms in an impedance testing circuit for the example of approximating a sine wave at a particular frequency. The approximated waveform (701) will have a 'stair-step' appearance in time since the voltage output of the DAC (318) can only operate with discrete values. A low-pass filter (317) may then be used to attenuate the high frequencies associated with these sharp transitions and smooth the waveform in time. The waveform output (702) of the low-pass filter (317) is a smoothed, more ideal, version of the waveform (701) that was approximated using the DAC (318). The voltage waveform at the output of the low-pass filter (317) may be converted to an AC current (703) by, for example, a series capacitor (315). If the voltage at the output of the low-pass filter (317) is V(t), then the current (325) passing through the capacitor is $C \cdot dV(t)/dt$, where C is the total series capacitance.

The total value of this series capacitance can be modified by any suitable mechanism, such as a binary control bus (316) from the digital controller (309). The control bus (316) selects the magnitude of the capacitance (315). This selection may be accomplished by using CMOS switches to connect multiple capacitors in parallel to adjust the effective total capacitance. These capacitors may have a range of values (e.g., C, 2C, 4C ... or C, 10C, 100C ... ) to allow a wide range of total capacitance to be selected. This configuration generally allows the magnitude of the AC current to be set since the current through the capacitance (315) is proportional to both the frequency of the DAC-generated signal and the magnitude of the total capacitance. For example, the waveform created by the DAC and low-pass filter can be a sine wave of amplitude A and frequency f: $V(t)=A \cdot \sin(2\pi ft)$. The current (325) through the series capacitor (315) will then be $C \cdot dV(t)/dt = C \cdot A \cdot f \cdot \cos(2\pi ft)$.

The resulting AC current (325) passing through the capacitor (315) may flow through a global wire (320) and through one of a series of digitally-control switches $S_0$-$S_{K-1}$ (304) onto a selected electrode input wire (214). These switches (304) may be implemented as standard CMOS switches or transmission gates, by way of example. If an electrode (202) is connected to one of the input bond pads (201), then this current will flow through this connected electrode and produce a voltage proportional to its impedance that can be measured by digitizing the signal from the appropriate amplifier (301). Only one of the switches (304) is closed at a time so that the current is directed to a single electrode. A command sent to the digital controller (309) selects which switch (304) (if any) is closed. When electrode impedance does not need to be measured, all the switches (304) are left open.

The use of the series capacitor (315) to introduce an impedance test current onto a selected electrode has the advantage of blocking any DC current that could potentially damage biological tissue or corrode the electrode over time.

Figure 5:
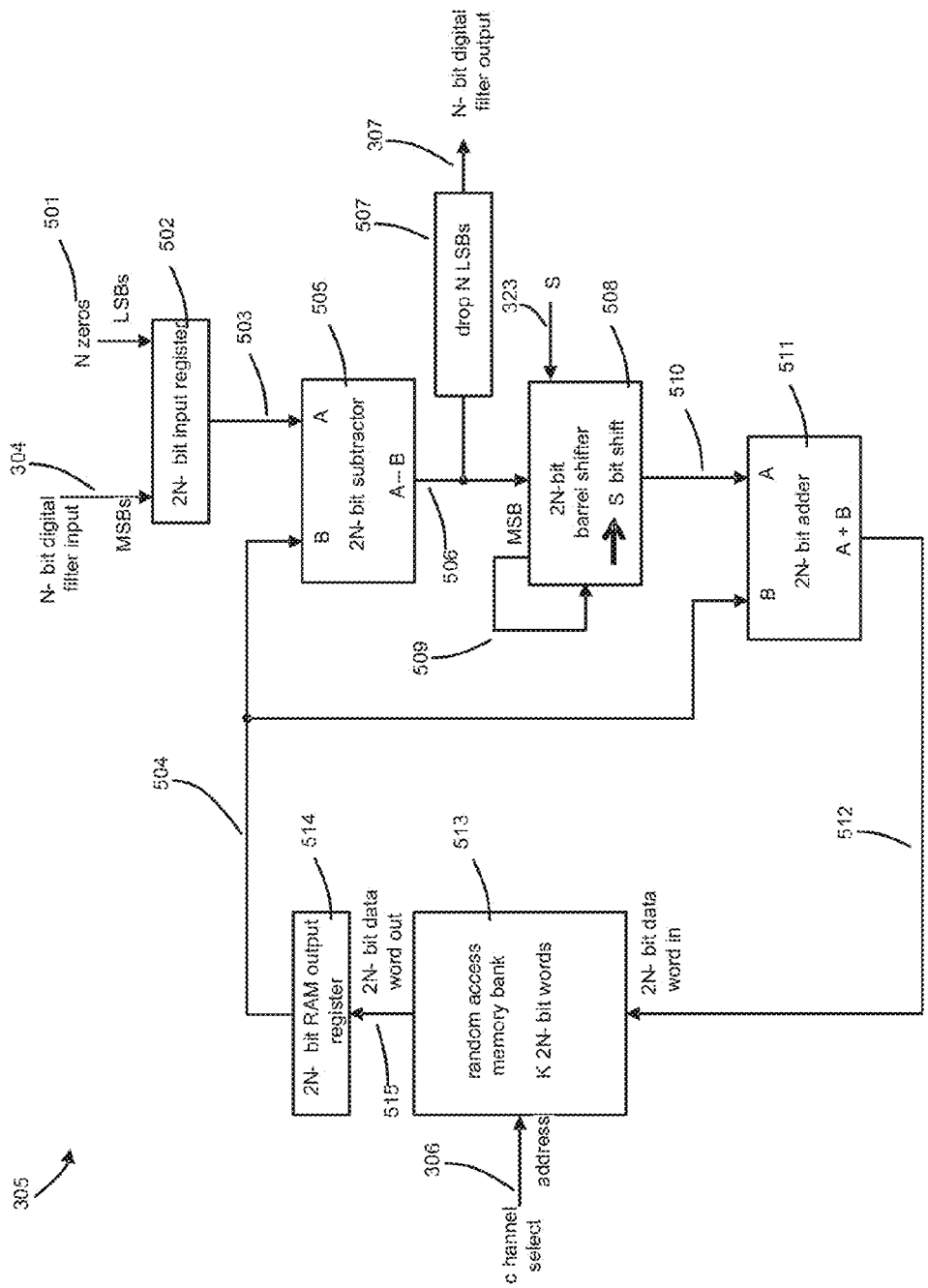
FIG. 5 is a block diagram of an example of the digital high-pass filter shown in FIG. 3.

FIG. 5 is a block diagram detailing the operation of the digital high-pass filter (305) of FIG. 3 in accordance with an example implementation. The filter (305) may be designed to use a single state variable for each amplifier channel and execute the following algorithm to implement a first-order high-pass filter with a cutoff frequency fc, operating at an ADC per-channel sampling rate of fs.

For an input signal from amplifier channel c (where c ranges from 0 to K) sampled at discrete times t, t+1, t+2, etc., $$\text{out}(c,t)=\text{in}(c,t)-\text{state}(c,t) \quad \text{[Equation 1]}$$

$$\text{state}(c,t+1)=\text{state}(c,t)+F \cdot [\text{in}(c,t)-\text{state}(c,t)] \quad \text{[Equation 2]}$$

where $F=1-\exp(-2\pi \cdot fc/fs)$

Equation 1 describes how the filter output is generated from the input ADC sample and the state variable for channel c. Equation 2 describes how the state variable for channel c is updated after each ADC sample from channel c. The filter variable F will always be a positive number between zero and one.

The input to the filter (305) may be an N-bit binary number from the ADC (303) in two's complement representation, for example. A 2N-bit register (502) may be configured to receive the N-bit input (304) into its N most significant bits (MSBs) and pad the N least significant bits (LSBs) with N zeros (501). Calculations internal to the digital filter may be performed at twice the ADC word width to minimize the effects of numerical rounding. The output of this register (503) may also be a 2N-bit binary number. This output number (503) may then be passed to a 2N-bit binary subtractor (505) that is operable to subtract a 2N-bit filter state variable (504) from the zero-padded input. The result of this subtraction (input minus state variable) is the output of the filter, but the output (307) may be truncated back down to N bits by dropping the N LSBs (507). These operations may be used to implement Equation 1 as presented above.

The filter state variable may next be updated according to Equation 2 as presented above. This update involves both a multiplication by a fractional constant (F) and an addition. The multiplication by F may be accomplished by using a barrel shifter (508) that shifts a 2N-bit binary word right (toward the LSB) by S bits, where S is set by a digital input bus (307). The MSB of the barrel shifter (509) may be preserved during shifts, preserving the sign of the two's complement number. Since shifting a binary number rightward by S bits is equivalent to dividing by $2^S$, only particular values for F are selected. In general, $F=1/2^S$, where S is a positive integer. This restricts the particular values of cutoff frequency that can be selected for this filter. However, the implementation of multiplication with a single barrel shifter greatly simplifies the hardware required to perform this operation and reduces the layout area consumed on a microchip. A general-purpose 2N-bit multiplier would be expensive both in terms of chip area and power consumption, but could be used.

The cutoff frequency of the filter fc will be:

$$fc = -(fs/2\pi) \cdot \ln(1-F) = -(fs/2\pi) \cdot \ln(1-\frac{1}{2}^5)$$

Since the digital high-pass filter (305) may be configured to only remove residual offsets contributed by the analog electronics on the microchip, the precise value of its cutoff frequency is not critical, so this coarse method is acceptable. The exact lower cutoff frequency of the amplifiers (301) can be set using the amplifier bandwidth control circuit (314) and associated control lines.

The output of the barrel shifter (510) may be connected to a 2N-bit adder (511) that adds this number to the present value of the state variable (504). This process may complete the filter computation and yield the updated value of the filter state variable (512) for the select amplifier channel. A random access memory (RAM) bank (513), or any other suitable memory, may be used to store the filter state variables for all K amplifier channels. All state variables may be stored with 2N-bit precision to reduce numerical rounding artifacts. A 'channel select' bus (306) may be used to select the appropriate address in the RAM bank. The present value of the state variable for the selected amplifier channel c may be read from the output of the RAM bank (515) and stored in the 2N-bit RAM output register (514) at the beginning of (or before) this process. The updated state variable value (512) may also be written back to the RAM once the filter calculation is complete.

By using a RAM for containing the filter state variables for all K amplifier channels, the arithmetic logic blocks ((505), (508), (511)) can be shared across all channels, saving chip area. If all amplifier channels are sampled regularly in 'round-robin' fashion, for example, then the output of the filter (307) will behave as if each channel had a separate digital filter unit.

Figure 6:
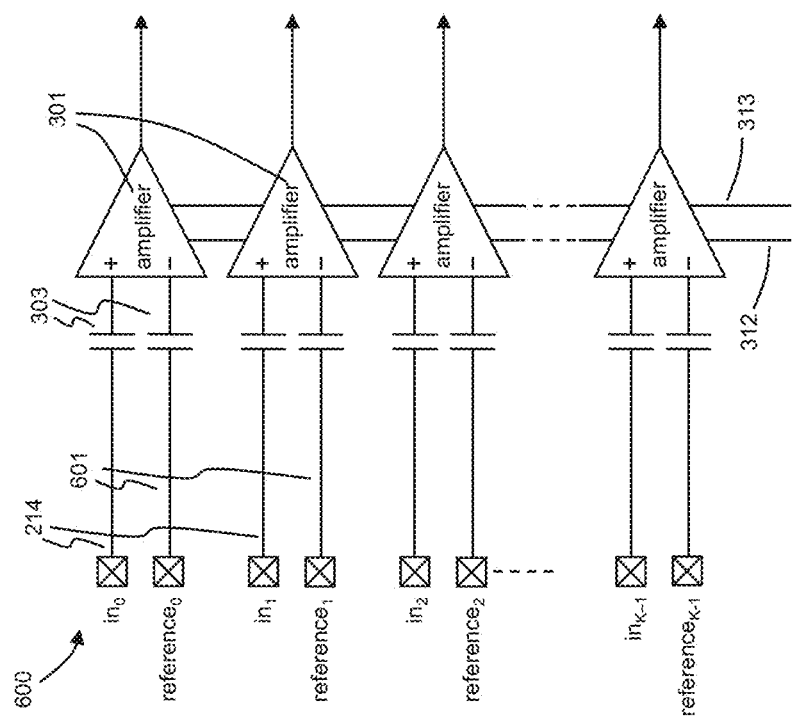
FIG. 6 is a diagram of an alternate configuration of amplifier input lines.

The bank of amplifiers (301) depicted in FIG. 3 may also be arranged in an alternate manner (600) as shown in FIG. 6 to have separate reference inputs (601) for the negative input of each amplifier. This arrangement may be useful in cases in which local bipolar recordings of potentials are necessary to reject large common-mode interfering signals, as with surface EMG recordings.

Figures 8A, 8B:
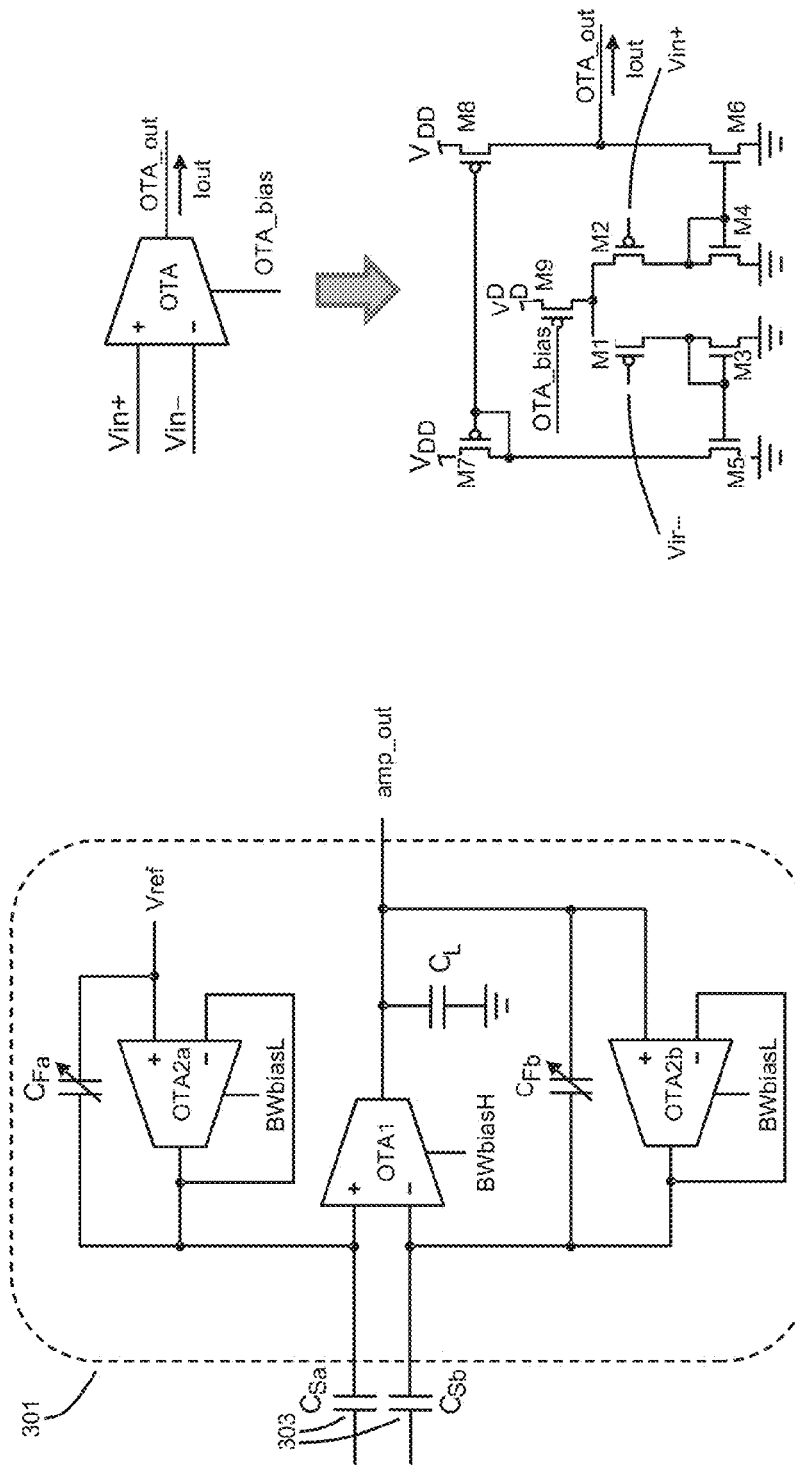
FIG. 8A is a schematic diagram of the band-pass amplifier and series capacitors of FIG. 3 in accordance with a specific implementation of the present invention.
FIG. 8B is a schematic diagram of one possible instantiation of an OTA (operational transconductance amplifier) that may be used as a building block in the construction of the band-pass amplifier of FIG. 8A.

FIG. 8A is a schematic diagram of one possible circuit for implementing the band-pass amplifier (301) of FIG. 3. The diagram includes series capacitors (303) used to block DC electrode offsets, as the value of these capacitors has a bearing on the amplifier gain. The series capacitors (303) and band-pass amplifiers together represent a specific implementation of a configurable receiver circuit for blocking DC offset from biopotential signals.

These two series capacitors (303) that connect electrode signals to the positive and negative inputs of the amplifier are labeled $C_{Sa}$ and $C_{Sb}$. In typical implementations, the capacitances of these devices will be equal: $C_{Sa} = C_{Sb} = C_S$.

This particular implementation of the band-pass amplifier (301) may be constructed from three operational transconductance amplifiers (OTAs). An OTA is a circuit that produces an output current that is proportional to a differential input voltage:

$$Iout = Gm(Vin+ - Vin-)$$

The constant of proportionality, Gm, has units of conductance (amperes/volt) and is called transconductance.

FIG. 8B shows one possible implementation of an OTA in CMOS (complementary metal oxide semiconductor) technology. The OTA may be powered from a DC voltage supply $V_{DD}$, which is typically in the range of 1 to 5 volts. The input voltages Vin+ and Vin- may be tied to the gates of pMOS (p-type metal oxide semiconductor) transistors M1 and M2. The sources of M1 and M2 are tied together in this implementation, forming a differential pair with a DC bias current sourced by pMOS transistor M9. The bias current may be controlled by the voltage OTA_bias, which is connected to the gate of transistor M9.

The transconductance (Gm) of the OTA is determined by the width and length of transistors M1 and M2, which are fixed when the circuit is fabricated; and by the bias current flowing from M9, which can be dynamically varied by changing the voltage of OTA_bias. A larger bias current will produce a larger value of Gm. The precise relationship between bias current and Gm is monotonic but complex, as the transistors M1 and M2 can operate in weak inversion mode (e.g., subthreshold), moderate inversion mode (e.g., near threshold), or strong inversion mode (e.g., above threshold). OTA_bias is a potent mechanism for controlling transconductance. In most implementations, varying the OTA_bias by less than one volt can change Gm by several orders of magnitude.

The voltage difference between Vin+ and Vin- determines how the bias current from M9 splits between M1 and M2. If Vin+ and Vin- are equal, the current will divide evenly between the left and right branches. Any imbalance in Vin+ and Vin- will steer more of the current toward one side or the other. Current mirrors formed by nMOS (n-channel metal oxide semiconductor) transistors M3 and M5, and by nMOS transistors M4 and M6 create copies of the currents flowing through M1 and M2, respectively. An additional current mirror formed by pMOS transistors M7 and M8 directs the current from the left and right branches of the circuit together onto the same node, effectively subtracting one current from the other.

The output current Iout is, therefore, approximately equal to the difference between the current flowing through M1 and the current flowing through M2. If the currents through M1 and M2 are equal, the output current will be approximately zero; positive or negative voltage differentials at the input will produce positive or negative currents at the output approximated by the equation shown above. Large differential input voltages will cause all the bias current from M9 to travel exclusively through either M1 or M2. In this case, the magnitude of the output current will saturate at the level of the bias current.

If desired, additional cascode transistors may be added in series with M6 and M8 to reduce the effects of finite drain conductance at the output node. The current mirrors may be designed with unequal transistor sizes to scale the transconductance. Other circuit configurations, such as a folded cascode topology or a telescopic topology, can be used to implement OTAs with roughly equivalent functionality as the current-mirror topology presented here. If desired, nMOS transistors can be used for the input differential pair, but in most CMOS technologies, pMOS devices are the best choice since they usually have lower 1/f noise or "flicker" noise.

The band-pass amplifier shown in FIG. 8A may be operable to use two types of OTAs: an OTA optimized for low input-referred noise (OTA1) and two nominally identical OTAs with reduced parasitic capacitances (OTA2a and OTA2b). Typically, OTA1 may be designed with wide and near-minimum-length transistors for devices M1 and M2, and long-gate-length transistors for device M3 through M8. These transistor sizes tend to reduce the input-referred noise of the OTA. OTA2a and OTA2b may be designed with relatively narrow and short transistors to reduce parasitic capacitance at the input and output of the OTA.

This band-pass amplifier (301) may also use at least three capacitors: a "load capacitor" $C_L$ tied from the output to ground and two feedback capacitors $C_{Fa}$ and $C_{Fb}$ connected from the positive input of the output of OTA2a and OTA2b, respectively. In this implementation, these capacitors always maintain identical values, so $C_{Fa}=C_{Fb}=C_F$. The feedback capacitors are variable (e.g., by connecting multiple smaller capacitors in parallel, using CMOS switches), but they always maintain equal values of capacitance. Feedback capacitor $C_{Fa}$ and the positive input of OTA2a may be connected to a DC voltage reference Vref produced by a bandgap voltage reference or other stable voltage source on the chip. This reference voltage determines the baseline output of the amplifier; AC signals swing above and below this level at the amp_out node.

The gain vs. frequency characteristics of this band-pass amplifier circuit are shown in FIG. 4. The pass band gain G (401) of the band-pass amplifier (301) is determined by the ratio of the series capacitance ($C_S$) to the feedback capacitance ($C_F$):

$$\text{Pass Band Gain} = G = C_S/C_F$$

By varying the value of the feedback capacitors, the gain of the amplifier can be changed (404) while maintaining constant amplifier input impedance.

The upper cutoff frequency (403) of the band-pass amplifier is a function of the transconductance of OTA1 (Gm1), the load capacitance ($C_L$), and the pass band gain (G):

$$\text{Upper Cutoff Frequency} = Gm1/(2\pi C_L G)$$

The upper cutoff frequency (403) can be selected by changing Gm1. This transconductance may be set by varying the bias voltage for OTA1, BWbiasH.

The lower cutoff frequency (402) of the band-pass amplifier is a function of the transconductance of OTA2a and OTA2b (Gm2) and the feedback capacitance ($C_F$):

$$\text{Lower Cutoff Frequency} = Gm2/(2\pi C_F)$$

The lower cutoff frequency (402) can be selected by changing Gm2. This transconductance may be set by varying the bias voltages of OTA2a and OTA2b, which are both tied to the node BWbiasL.

By changing the voltages on the BWbiasH and BWbiasL lines, the upper and lower cutoff frequencies of the amplifier can be varied by more than an order of magnitude. Referencing FIG. 3, the BWbiasH line corresponds to the upper cutoff frequency control line (313); the BWbiasL line corresponds to the lower cutoff frequency control line (312).

By changing the value of feedback capacitors $C_{Fa}$ and $C_{Fb}$, the pass band gain may be selected. The gain control line (328) selects the value of $C_{Fa}$ and $C_{Fb}$.

The equations above show an interaction between gain and bandwidth, which can be implemented in software (and/or hardware) so that the proper control signals are used to select the desired amplification parameters.

While FIG. 8A-B show the band-pass amplifier implemented as an OTA-based circuit, the band-pass amplifier could also be implemented as a switched-capacitor filter or a chopper amplifier. Multi-stage amplifiers may also be used to separate the gain and filtering operations into separate amplification stages.

The electrophysiology monitoring system may be used in any suitable manner. FIG. 9 is a flowchart illustrating one embodiment of a process for biopotential sensing (900) using embodiments of the sensing device described herein. This procedure may be implemented by one or more components of the sensing device, for example, of FIG. 3 within the context of the system of FIG. 2. Initially, it may be determined whether a frequency and/or gain parameter has been received in operation 902. For instance, a command for setting a lower frequency cutoff value may be received from analyzer 203 into the controller 309 of the sensing device 300 via data in line 210 of a serial bus. This parameter setting may then be stored in operation 904 and converted into one or more signals for setting a frequency or gain characteristic of a received biopotential signal in operation 906. For instance, the controller 309 sends a binary lower frequency cutoff value to the amplifier bandwidth control circuit 314, which generates control signals input to the band-pass amplifiers 301.

It may then also be determined whether a command for sensing a biopotential signal has been received in operation 908. In the illustrated example, multiple commands for cyclically processing each channel's biopotential signal may be received by controller 309 from an analyzer computer 203 via a serial bus. When a command for sensing a biopotential signal is received, one or more signals for selecting one or more channels to receive and amplify corresponding biopotential signals may be generated in operation 910. For instance, controller 309 generates a channel select signal to select a particular channel, and this channel select signal is output to MUX 302 and digital high pass filter 305.

For each selected channel, the DC offset may be removed from the sensed biopotential signal, and such signal is amplified based on the generated frequency and/or gain signals in operation 912. For example, the selected amplifier 301 band pass filters the sensed biopotential signal based on a higher and lower cutoff frequency signal. Each amplified biopotential signal may then be converted into a digitized representation (e.g., by ADC 303) and any additional DC offsets are removed from such digitized representation (e.g., 305) in operation 914. The digitized representation (without the DC offset) may then be output to an analyzer (e.g., 203) in operation 916.

In this illustrated embodiment, if no command for sensing a signal has been received, it may then be determined whether an impedance monitoring command has been received in operation 918. If no command has been received, the process 900 may be repeated. If an impedance monitoring command has been received, an AC current waveform may be generated on a selected electrode in operation 920. For instance, the controller receives commands for generating AC voltage waveforms by DAC 318 and low-pass filter 317 and for setting the capacitance values of capacitors 315 to generate particular AC current waveforms. Operations 910-916 may then be performed to measure the resulting impedance (e.g., voltage) signals, which are output to the analyzer to determine impedance. Either the sensed or detected signals or an AC voltage waveform for the particular electrode, whose amplitude is proportional to the electrode's impedance value, may be output to the analyzer device. It is also contemplated that the controller may be configured to calculate impedance based on the digitized representation of the measured signal and output such calculated impedance to the analyzer. The process 900 may be repeated.

Although not shown, the sensing device may output various data in response to "read" commands received by the external analyzer. For instance, the controller of the sensing device may be configured to store each biopotential result at a particular memory location. The controller may then output a particular result in response to a read command for a particular result that is associated with a particular memory address. Alternatively, the controller may automatically output a result whenever such result is generated.

Certain embodiments of the present invention provide a device having reconfigurable bandwidth that can be configured to match the signals of interest so as to optimize the signal-to-noise ratio of the acquisition system. In some applications, the amplifier bandwidth is reconfigured dynamically to match the characteristics of the observed biopotential signals, isolate various signals of interest, block undesired interfering signals, or otherwise optimize the signal recorded from the electrodes.

Certain embodiments also remove offset from the raw electrode signal so that the receiving gain amplifier will saturate at its minimum or maximum output level due to an offset voltage. Since certain embodiments of the present invention do not use low-gain DC-coupled amplifiers to amplify both the biopotential signal and the electrode offset, this approach does not require high-resolution ADCs (e.g., 24-bit) with very low levels of input-referred noise to capture a tiny voltage signal, which has only been amplified by a small gain. That is, lower resolution ADCs may be used (e.g., 16) with lower input noise so that less power and microchip layout area are consumed, as compared to higher resolution ADCs (e.g., 24-bit).

Certain embodiments integrate biosensing and impedance monitoring mechanisms. In certain clinical and scientific applications, it is important to monitor the impedance of biopotential electrodes to track electrode condition and detect electrode failure. Monitoring system embodiments provide an impedance measuring function in a single biopotential recording device.

Additionally, certain embodiments provide a fully integrated, single-chip approach that allows the bandwidth of the amplifiers to be reconfigured by software (e.g., to isolate various signals of interest in a complex biopotential waveform) and consumes less size and mass than integrated amplifiers that are configurable through off-chip hardware components, such as resistors, having selectable fixed values. There is also a long-term trend toward miniaturization of implantable and wearable medical devices, and electrophysiology instrumentation. Combining all biopotential sensing capabilities onto one integrated circuit, or microchip, reduces the size, mass, and power requirements in these applications.

The biosensing system may be controlled by any suitable combination of hardware and/or software (e.g., for implementing a controller and/or analyzer). For instance, a system may include any number of finite state machines, programmable modules, microcontrollers, or processors (also referred to as central processing units, or CPUs) that are coupled to any number of storage or memory devices. The CPU (or other analyzer or controller device) may be of various types, including microcontrollers and microprocessors such as programmable devices (e.g., CPLDs and FPGAs) and unprogrammable devices such as gate array ASICs or general-purpose microprocessors. As is well known in the art, a storage device generally acts to transfer data and instructions to and from the CPU (or other analyzer or controller device). Each storage device may include any suitable computer-readable media such as those described herein. A mass storage device may also be coupled bi-directionally to the CPU (or other analyzer or controller device) and provide additional data storage capacity and may include any of the computer-readable media described herein. A mass storage device may be used to store programs, data and the like and is typically a secondary storage medium, such as a hard disk. It will be appreciated that the information retained within the mass storage device, may, in appropriate cases, be incorporated in standard fashion as part of primary storage as virtual memory. A specific mass storage device such as a CD-ROM may also pass data unidirectionally to the CPU (or other analyzer or controller device).

The CPU (or other analyzer or controller device) may also be coupled to an interface that connects to one or more input/output devices such as video monitors or displays, track balls, mice, keyboards, microphones, touch-sensitive displays, transducer card readers, magnetic or paper tape readers, tablets, styluses, voice or handwriting recognizers, or other well-known input devices such as, of course, other computers. Finally, the CPU (or other analyzer or controller device) optionally may be coupled to an external device such as a database or a computer or telecommunications network using an external connection. With such a connection, it is contemplated that the CPU (or other analyzer or controller device) might receive information from the network, or might output information to the network in the course of performing the method steps described herein.

Because such information and program instructions may be employed to implement the systems/methods described herein, the present invention relates to machine readable storage media that include program instructions, state information, etc. for performing various operations described herein. Examples of machine-readable storage media include, but are not limited to, magnetic media such as hard disks, floppy disks, and magnetic tape; optical media such as CD-ROM disks; magneto-optical media such as floptical disks; and hardware devices that are specially configured to store and perform program instructions, such as ROM and RAM. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A device for monitoring biopotentials of biological tissue through a plurality of electrodes, the device comprising:
 a configurable receiver circuit having a plurality of channels for receiving a plurality of biopotential signals from a biological tissue via a plurality of inputs coupled with the electrodes, each channel being configured to substantially remove a DC (direct current) offset from a corresponding one of the plurality of biopotential signals and then band-pass amplify the corresponding one of the biopotential signals at a configurable particular frequency range based on one or more frequency control signals;
 a controller circuit operable to receive commands for configuring or reconfiguring one or more frequency characteristics pertaining to receiving each biopotential signal;
 an impedance measurement module for generating a capacitively-coupled AC (alternating current) current waveform, having an amplitude and frequency, that is applied to a particular input coupled to a particular channel to measure a voltage signal received at the particular channel in response to the AC current waveform applied to the particular input,
 wherein the controller is further configurable to program the impedance measurement module to generate the capacitively-coupled AC current waveform to be applied to the particular selected input so as to monitor the impedance of the corresponding one of the electrodes by calculating the impedance based on the measured voltage signal received at the particular channel, wherein the controller is further configurable to automatically generate the one or more frequency control signals based on the commands and output the one or more frequency control signals to the configurable receiver circuit, wherein the controller is further configurable to output a representation of each biopotential signal and a representation of the calculated impedance to an analyzer device that is configured to analyze the representation of each biopotential signal and the representation of the calculated impedance.

2. The device of claim 1, further comprising:

a multiplexer (MUX) coupled to the channels of the configurable receiver circuit so as to output a selected one of the amplified biopotential signal based on a received channel select signal; and an analog to digital converter (ADC) for receiving the selected amplified biopotential signal from the MUX and converting the selected amplified biopotential signal to a digitized representation of the selected amplified biopotential signal, wherein the controller is further operable to output a channel selection signal to the MUX indicative of which channel the MUX is to output one of the biopotential signals to the ADC.

3. The device of claim 2, wherein the configurable receiver circuit comprises:

a configurable band-pass amplifier in each channel for amplifying the corresponding biopotential signal, wherein the one or more frequency characteristics comprise a lower cutoff frequency and/or an upper cutoff frequency for each amplified signal; and a capacitor at each input of each amplifier for removing the DC offset from each corresponding biopotential signal.

4. The device of claim 3, further comprising:

a digital high pass filter for receiving the digitized representation of the selected signal output from the ADC and removing one or more residual DC offsets introduced in the received digital representation based on a cutoff frequency signal received by the digital high pass filter, wherein the one or more residual DC offsets include a DC offset that is introduced by the amplifiers, MUX, or ADC, wherein the commands further include a command for reconfiguring a cutoff frequency for the digital high pass filter, wherein the controller is further configurable to automatically generate a cutoff frequency control signal based on the command for reconfiguring the cutoff frequency and outputting the cutoff frequency control signal to the digital high pass filter.

5. The device of claim 4, wherein the commands include a command for reconfiguring a gain of each biopotential signal input to each amplifier so that the amplified signal output from each amplifier has a signal level that falls within the range of the ADC.

6. The device of claim 2, wherein the ADC has a resolution that is between 10 to 16 bits.

7. The device of claim 1, further comprising a bus that is communicatively coupled to the controller and the bus being arranged for receiving a plurality of commands that are transmitted to the controller and for reconfiguring the amplitude and frequency of the AC current waveform generated by the impedance measurement module, and wherein the controller is further configurable to automatically program the impedance measurement module to generate one or more AC waveform control signals based on the commands for reconfiguring the amplitude and frequency of the one or more AC waveform control signals generated by the impedance measurement module.

8. The device of claim 7, wherein the controller is further configured to receive, via the bus, a plurality of commands for reconfiguring the amplitude and/or frequency so as to generate a plurality of AC current waveforms having a plurality of frequencies for performing impedance spectroscopy.

9. The device of claim 7, wherein the impedance measurement module comprises:

a digital to analog converter (DAC) having an input for receiving a plurality of digital voltage values, via the bus, based on a first one of the AC waveform control signals, wherein the DAC is operable to convert the digital voltage values into a plurality of analog voltage values and output the analog voltage values;

a low pass filter having an input for receiving the plurality of analog voltage values output by the DAC, wherein the low pass filter is operable to attenuate frequencies that are higher than a predefined value so as to output an AC voltage waveform, which is based on the received analog voltage values, to the particular input that is coupled to the particular electrode; and one or more capacitors coupled to the output of the low pass filter and arranged to receive a second one of the AC waveform control signals that sets a capacitance value of the one or more capacitors so as to convert the AC voltage waveform into an AC current waveform having substantially all DC current removed from the AC current waveform that is input into the particular electrode.

10. The device of claim 1, wherein the analyzer device is in the form of a computer or processor coupled via a bidirectional bus to the controller.

11. The device of claim 1, wherein the configurable receiver circuit and the controller circuit are integrated together on a single microchip.

* * * * *